United States Patent [19]

Hachisuka et al.

[11] Patent Number: 5,510,527
[45] Date of Patent: Apr. 23, 1996

[54] ACID CHLORIDE

[75] Inventors: Hisao Hachisuka; Katsuhide Kojima; Yutaka Nakazono; Masahiko Hirose; Yasuo Kihara; Masatoshi Maeda; Hisashi Ikebata; Kenji Matsumoto, all of Osaka, Japan

[73] Assignee: Nitto Denko Corporation, Osaka, Japan

[21] Appl. No.: 202,121

[22] Filed: Feb. 25, 1994

Related U.S. Application Data

[62] Division of Ser. No. 7,763, Jan. 22, 1993, Pat. No. 5,336,409.

[30] Foreign Application Priority Data

Jan. 22, 1992 [JP] Japan .................................. 4-32536
Jul. 29, 1992 [JP] Japan .................................. 4-202384
Aug. 20, 1992 [JP] Japan .................................. 4-221348

[51] Int. Cl.$^6$ .................................................. B01D 71/56
[52] U.S. Cl. ................ 562/867; 210/500.37; 210/500.38
[58] Field of Search ................................ 210/490, 500.37, 210/500.38; 427/245; 568/341; 430/260; 562/840, 864, 866, 867

[56] References Cited

U.S. PATENT DOCUMENTS

| | | | |
|---|---|---|---|
| 4,242,278 | 12/1980 | Martin et al. | 568/341 |
| 4,626,468 | 12/1986 | Sundet | 210/315.5 |
| 4,828,708 | 5/1989 | Bray | 210/654 |
| 5,258,203 | 11/1993 | Arthur | 427/245 |
| 5,298,361 | 3/1994 | Bonham | 430/260 |

FOREIGN PATENT DOCUMENTS

| | | |
|---|---|---|
| 0361092 | 4/1990 | European Pat. Off. . |
| 2462196 | 3/1979 | Germany . |

*Primary Examiner*—Frank Spear
*Attorney, Agent, or Firm*—Sughrue, Mion, Zinn, Macpeak & Seas

[57] ABSTRACT

An acid chloride, bicyclo[2,2,2]oct-7ene-(2α,3β,5α,6β)tetracarbonyl chloride ($C_{12}H_8O_4Cl_4$) represented by the following formula:

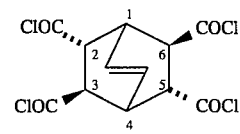

1 Claim, 4 Drawing Sheets

ACID CHLORIDE

This is a divisional of application Ser. No. 08/007,763 filed Jan. 22, 1993, now U.S. Pat. No. 5,336,409.

FIELD OF THE INVENTION

The present invention relates to a composite reverse osmosis membrane for selectively separating a desired component from a liquid mixture, and more particularly to a composite reverse osmosis membrane having a high permeation flux and a high salt rejection, which comprises a thin membrane comprising a crosslinked polyamide having a specific structure provided on a microporous supporting membrane. The composite reverse osmosis membrane is suitable for the production of ultrapure water, the desalination of brine or seawater, etc., and can contribute to close waste water by removing a pollution source or recovering an effective material from dyed waste water, an electrodeposition coating composition waste water, etc., which are stains of causing pollutions.

The present invention also relates to a novel acid chloride, that is, bicyclo[2,2,2]oct-7ene(2α, 3β,5α,6β)-tetracarbonyl chloride exhibiting excellent performances as polymeric material-producing raw materials such as crosslinking agents, esterifying agents, amidating agents, acylating agents, etc.

BACKGROUND OF THE INVENTION

Hitherto, as a reverse osmosis membrane having a structure different from that of an asymmetric reverse osmosis membrane, a composite reverse osmosis membrane comprising a microporous supporting membrane having formed thereon an active thin membrane having substantially selective separation property is known.

At present, as such a composite reverse osmosis membrane, many composite reverse osmosis membranes wherein a thin membrane comprising a polyamide obtained by an interfacial polymerization of a polyfunctional aromatic amine and a polyfunctional aromatic acid halide is formed on a supporting membrane are known as described in, e.g., JP-A-55-147106, JP-A-62-121603, JP-A-63-218208, and JP-A-2-187135 (the term "JP-A" as used herein means an "unexamined published Japanese patent application").

Also, composite reverse osmosis membranes wherein a thin membrane comprising a polyamide obtained by an interfacial polymerization of a polyfunctional aromatic amine and polyfunctional alicyclic acid halide is formed on a supporting membrane are known as described in, e.g., JP-A-62-258705 and JP-A-63-218208.

The above-described composite reverse osmosis membranes have a high desalinating property and a high water permeability, but in a recent ultrapure water production system, it has been required to increase the purity of water by a membranes only by reducing the amount of ion-exchange resins used. For example, it has-been required to reduce the electrical conductivity of water to the same extent as the case of using ion-exchange resins by using reverse osmosis membranes in two stages. Also, with the increase of the capacity of semiconductors, cleaner ultrapure water has been required and for satisfying the requirement, the conventional composite reverse osmosis membranes are insufficient and a composite reverse osmosis membrane having a higher desalting property and a higher water permeability has been demanded.

Also, aromatic or alicyclic polyvalent acid chlorides are widely used as polymeric material-producing raw materials such as crosslinking agents, condensing agents, etc. An aromatic polyvalent acid chloride generally forms a rigid condensation product but has problems that the reactivity is poor, etc. On the other hand, an allcyclic polyvalent acid chloride shows a good reactivity but the condensation product is flexible, causing a problem according to the use.

Thus, from the standpoint of forming a rigid condensation product while maintaining the good reactivity of an alicyclic polyvalent acid chloride, a polyvalent acid chloride comprising a bicyclo ring has been given attention.

However, the polyvalent acid chloride comprising a bicyclo ring has problems in the stability of the acid chloride, the danger in the case of producing (synthesizing) the acid chloride, the troublesomeness of the production (synthesis) steps, the low yield, and the difficulty of obtaining the raw material as an alicyclic polyvalent acid chloride. Thus, the production of such a polyvalent acid anhydride has scarcely practiced.

Furthermore, different from the aromatic polyvalent acid chloride, the polyvalent acid chloride include various kinds of isomers and from the dispersion of the reactivities among the isomers, there is a problem that a stable condensation product is not obtained in the case that the ratio of the isomers is different.

However, recently, the investigations on a polyvalent acid chloride comprising a bicyclo ring which is considered to have both the advantages of an aromatic polyvalent acid chloride and an alicyclic polyvalent acid chloride have been proceeded, and the interest of such a polyvalent acid chloride as polymeric material-producing raw materials such as crosslinking agents, condensing agents, esterifying agents, amidating agents, acylating agents, etc., has been increased.

Thus, in the industry, the development of an excellent novel acid chloride which can be safely and widely utilized as polymeric material-producing raw materials has been desired.

SUMMARY OF THE INVENTION

One object of the present invention is to provide a composite reverse osmosis membrane having both a high salt rejection and a high flux, and capable of desalinating with a practically usable high salt rejection at a relatively low pressure.

Another object of the present invention is to provide an excellent novel acid chloride which can be safely and widely utilized.

That is, according to the 1st embodiment of the present invention, there is provided a composite reverse osmosis membrane comprising a thin membrane and microporous supporting membrane supporting the thin membrane, wherein the thin membrane mainly comprises a crosslinked polyamide comprising (a) an amine component containing at least one member selected from the group consisting of substantially monomeric amine compounds each having at least two primary and/or secondary amino groups, and (b) an acid halide component containing at least one member selected from the group consisting of substantially monomeric cyclic acid halide compounds each having at least two acid halide groups and comprising at least two rings.

Also, according to the 2nd embodiment of the present invention, there is provide a novel acid chloride, bicyclo[2, 2,2]oct-7ene-(2α, 3β,5α,6β)-tetracarbonyl chloride which is suitably used for making the composite reverse osmosis membrane as the cyclic acid halide compound.

DETAILED DESCRIPTION OF THE INVENTION

Figure 1:
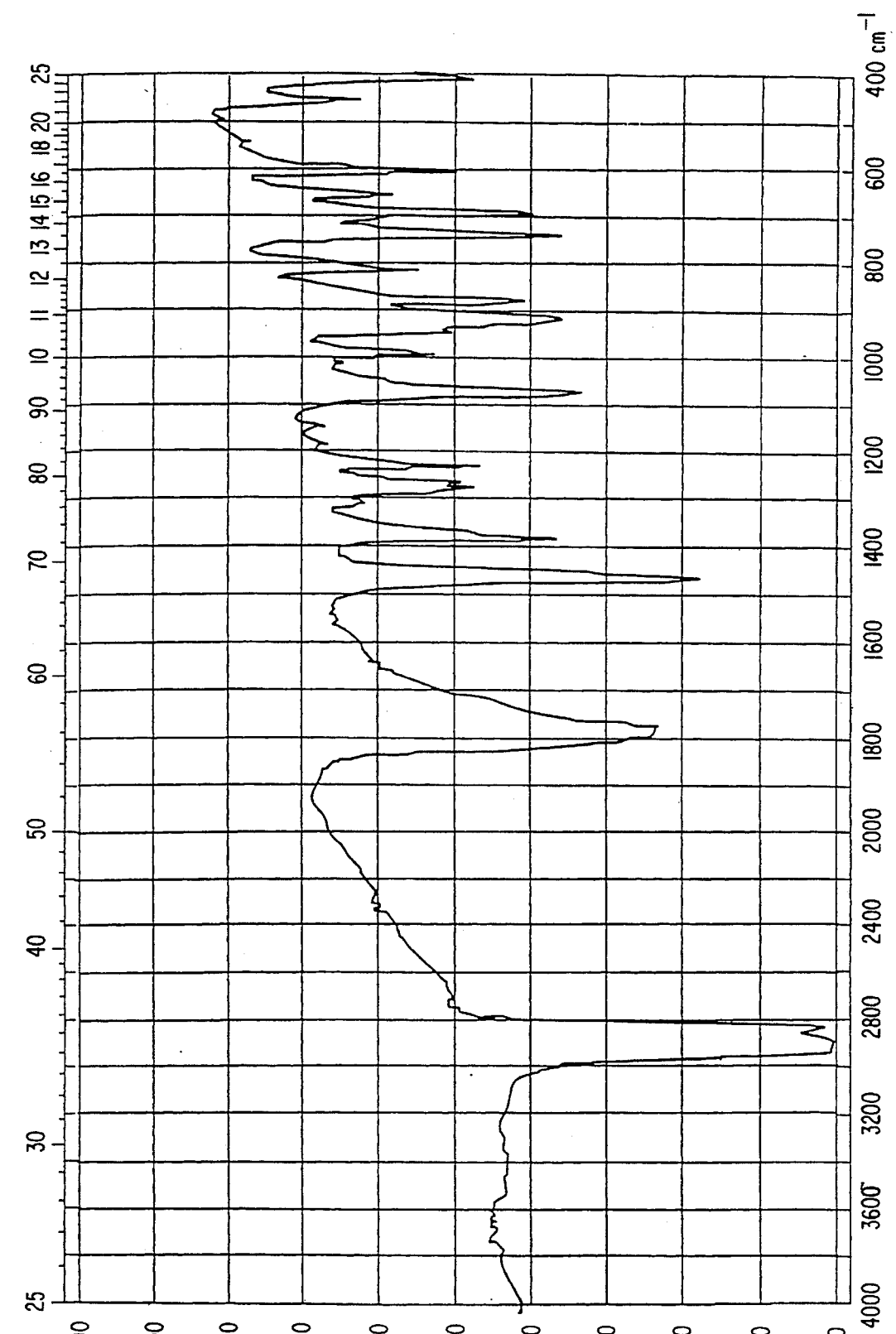
FIG. 1 is an infrared absorption spectral (Nujol mull method) chart of bicyclo[2,2,2]oct-7ene-(2α, 3β,5α,6β)-tetracarbonyl chloride which is the novel acid chloride of the present invention.

There is no particular restriction on the amine component (a) being used in the present invention if the amine component is a polyfunctional amine containing at least one member selected from the group consisting of substantially monomeric amine compounds each having at least two primary and/or secondary amino groups, and aromatic, aliphatic, and alicyclic polyfunctional amines can be used.

Examples of the aromatic polyfunctional amine are m-phenylenediamine, p-phenylenediamine, 1,3,5-triaminobenzene, 3,5-diaminobenzoic acid, 2,4-diaminotoluene, 2,4-diaminoanosol, amidol, and xylenediamine.

Examples of the aliphatic polyfunctional amine are ethylenediamine, propylenediamine, and tris(2-amino-ethyl)amine.

Examples of the alicyclic polyfunctional amine are 1,3-diaminocyclohexane, 1,2-diaminocyclohexane, 1,4-diaminocyclohexane, piperazine, 2,5-dimethylpiperazine, and 4-aminomethylpiperazine.

These polyfunctional amines may be used alone or as mixtures thereof.

There is no particular restriction on the acid halide component (b) being used in the present invention if it is the acid halide containing at least one member selected from the group consisting of substantially monomeric cyclic acid halide compounds each having at least two acid halide groups and comprising at least two rings. Such a cyclic acid halide compound may further contain at least one double bond in the molecule.

Examples of such a cyclic acid halide compound are bicyclo[2,2,2 ]oct-7ene-2,3,5,6-tetracarbonyl chloride represented by the formula

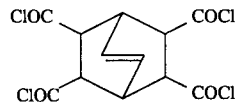

3,5,6-tricarboxychloronorbornane-2-acetic acid chloride, and tetracyclo[4,4,1,0$^{2,5}$,0$^{7,10}$]undeca-3,8-diene-3,4,8,9-tetacarboxylic acid chloride.

The acid halide component (b) may have in the molecule thereof an atom such as —O—, —S— or —NR— wherein R is hydrogen or an alkyl group. Examples thereof include 7-oxabicyclo[2,2,1]heptane-2,3,5,6-tetracarboxylic acid chloride, 5,5'-thiobis(norbornane-2,3-dicarboxylic acid chloride), and the like.

Each of these compounds can be obtained by hydrolyzing the corresponding ester and anhydride and reacting the hydrolyzed product and phosphorus pentachloride. For example, bicyclo[2,2,21]oct-7ene-2,3,5,6-tetracarboxylic acid chloride described above can be obtained by hydrolyzing bicyclo[2,2,2oct-7ene-2,3,5,6-tetracarboxylic anhydride and reacting the hydrolyzed product and phosphorus pentachloride.

Furthermore, by recrystallizing bicyclo[2,2,2]-oct-7ene-2,3,5,6-tetracarbonyl chloride thus obtained using a mixed solvent of benzene and hexane, bicyclo[2,2,2]oct-7ene-(2α, 3β,5α,6β)-tetracarbonyl chloride, which is a trans form, represented by the following formula can be obtained.

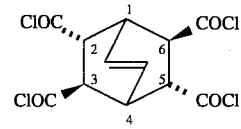

The trans form, bicyclo[2,2,2]oct-7ene-(2α, 3β,5α,6β)-tetracarbonyl chloride represented by the above formula is a novel acid chloride, which will be described hereinafter in detail.

As the acid halide component (b) being used in the present invention, the above-described cyclic acid halide compound may be used alone or may be used together with other acid halide compound, such as an aliphatic polyfunctional acid halide, an alicyclic polyfunctional acid halide, or an aromatic polyfunctional acid halide.

Examples of such an aromatic polyfunctional acid halide are dihalides such as terephthalic acid halide, isophthalic acid halide, 1,3-cyclohexanedicarboxylic acid halide, 1,4-cyclohexanedicarboxylic acid halide, biphenyl-2,2'-dicarboxylic acid halide, 2,6-naphthalenedicarboxylic acid halide, 2,7-naphthalenedicarboxylic acid halide, p-phenylenediacetic acid halide, m-phenylenediacetic acid halide, m-phenylenediacetic acid halide, p-phenylenediacetic acid halide, etc., and trihalides such as trimesic acid halide, 1,3,5-cyclohexanetricarboxylic acid halide, etc. In the present invention, trimesic acid chloride, isophthalic acid chloride, terephthalic acid chloride, biphenyl-2,2'-dicarboxylic acid chloride, 2,6-naphthalenedicarboxylic acid chloride, 2,7-naphthalenedicarboxylic acid chloride, etc., are preferably used.

Examples of the aliphatic polyfunctional acid halide are difunctinal aliphatic acid halides such as glutaryl halide, adipoyl halide, sebacoyl halide, etc., trifunctional or higher functional aliphatic acid halides such as 1,2,3-propanetricarboxylic acid trichloride, 1,2,4-butanetricarboxylic acid trichloride, 1,2,3,4-butanetetracarboxylic acid tetrachloride, 1,2,4,5-pentanetetracarboxylic acid tetrachloride, etc., and mixtures thereof.

Examples of the alicyclic polyfunctional acid halide are 2,3,4,5-cyclopentanetetracarboxylic acid chloride, 1,2,4-cyclopentanetricarboxylic acid chloride, 1,2,3,4-cyclo-butanetetracarboxylic acid chloride, 1,3,5-cyclohexanetricarboxylic acid chloride, 1,2,3,4,5,6-cyclohexanecarboxylic acid chloride, and tetrahydrofuran-2,3,4,5-tetracarboxylic acid chloride.

In the present invention, by interfacial-polymerizing the amine component (a) and the acid halide component (b), a composite reverse osmosis membrane comprising a thin membrane of a crosslinked polyamide formed on a microporous supporting membrane is obtained.

In the present invention, there is no particular restriction on the microporous supporting membrane for supporting the thin membrane if the microporous membrane can support the thin membrane, and there are, for example, polysulfone; polyaryl ether sulfones such as polyether sulfone, etc.; polyimide; and polyvinylidene fluoride. In particular, from the point of the chemical, mechanical, and thermal stabilities, the microporous supporting membrane comprising polysulfone or polyaryl ether sulfone is preferably used.

The microporous supporting membrane usually has a thickness of from about 25 to 125 μm, and preferably from about 40 to 75 μm although the thickness is not always limited to the range.

More practically, the composite reverse osmosis membrane can be obtained by forming a 1st layer comprising an aqueous solution containing the amine component (a) on a microporous supporting membrane, then forming a layer comprising water-immiscible organic solvent solution containing the acid halide component (b) on the 1st layer, and carrying out the interfacial polycondensation to form a thin membrane comprising a crosslinked polyamide on the microporous supporting membrane.

For facilitating the film-formation and improving the performance of the composite reverse osmosis membrane obtained, the aqueous solution containing the polyfunctional amine can further contain a water-soluble polymer such as polyvinyl alcohol, polyvinyl pyrrolidone, polyacrylic acid, etc., and a polyhydric alcohol such as sorbitol, glycerol, etc.

Also, the amine salts such as tetraalkyl ammonium halides, the salts of trialkylamines and organic acids, etc., described in JP-A-2-187135 can be suitably used for the aqueous solution of the polyfunctional amine in the points of facilitating the film-formation, improving the absorption property of the microporous supporting membrane for the amine solution, accelerating the condensation reaction, etc.

The aqueous solution of the polyfunctional amine can contain a surface active agent such as sodium dodecylbenzenesulfonate, sodium dodecylsulfate, sodium laurylsulfate, etc. These surface active agents are effective for improving the wetting property of the microporous supporting membrane with the aqueous solution of the polyfunctional amine. Furthermore, for accelerating the polycondensation reaction at the interface, it is useful to use sodium hydroxide or sodium tertiary phosphate capable of removing hydrogen halides formed by the interfacial reaction or to use a quaternary ammonium salt, an acylating catalyst, a phase-transfer catalyst, etc., as a catalyst.

As the organic solvent for preparing the water-immiscible organic solvent solution containing the acid halide component, organic solvents which dissolve well the acid halide being used and do not dissolve the microporous supporting membrane can be used without any restriction. Examples of such an organic solvent are hydrocarbons such as n-hexane, cyclohexane, etc., and halogenated hydrocarbons such as Freon (trade name, made by E. I. du Pont de Nemours & Co., Inc.) including trichlorotrifluoroethane.

In the organic solvent solution containing the acid halide and the aqueous solution containing the polyfunctional amine, there are no particular restrictions on the concentrations of the acid halide and the polyfunctional amine, but the concentration of the acid halide is usually from 0.01 to 5% by weight, and preferably from 0.05 to 1% by weight and the concentration of the polyfunctional amine is usually from 0.1 to 10% by weight, and preferably from 0.5 to 5% by weight.

The aqueous solution containing the polyfunctional amine is coated on the microporous supporting membrane, after further coating thereon the organic solvent solution containing the cyclic acid halide compound, each excessive solution is removed, and the coated layers are dried by heating to a temperature of usually from about 20° to 150° C., and preferably from about 70° to 130° C., for from about 1 to 10 minutes, and preferably from about 2 to 8 minutes to form a water-permeable thin membrane comprising a crosslinked polyamide. The thickness of the thin membrane is in the range of usually from about 0.05 to 1 μm, and preferably from 0.15 to 0.5 μm.

The salt rejection performance of the composite reverse osmosis membrane of the present invention can be further improved by subjecting the composite reverse osmosis membrane to a chlorine treatment with hypochlorous acid, etc., as described in JP-B-63-36803 (the term "JP-B" as used herein means an "examined published Japanese patent application").

Then, the novel acid chloride having a simple isomer structure, bicyclo[2,2,2]oct-7ene-(2α, 3β,5α,6β)-tetracarbonyl chloride, which is the 2nd embodiment of the present invention, is described in detail.

The novel acid chloride which is the 2nd embodiment of the present invention is bicyclo[2,2,2]oct-7ene-(2α, 3β,5α, 6β)-tetracarbonyl chloride represented by the following formula:

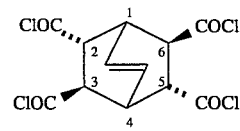

The novel acid chloride, bicyclo[2,2,2]oct-7ene-(2α, 3β,5α,6β)-tetracarbonyl chloride is a white to light-brown crystal and the melting point thereof is 96° C.

The absorption wave number ($cm^{-1}$) of the infrared absorption spectrum of the novel acid chloride measured by a Nujol mull method was 1790(s) (see FIG. 1).

Figure 2:
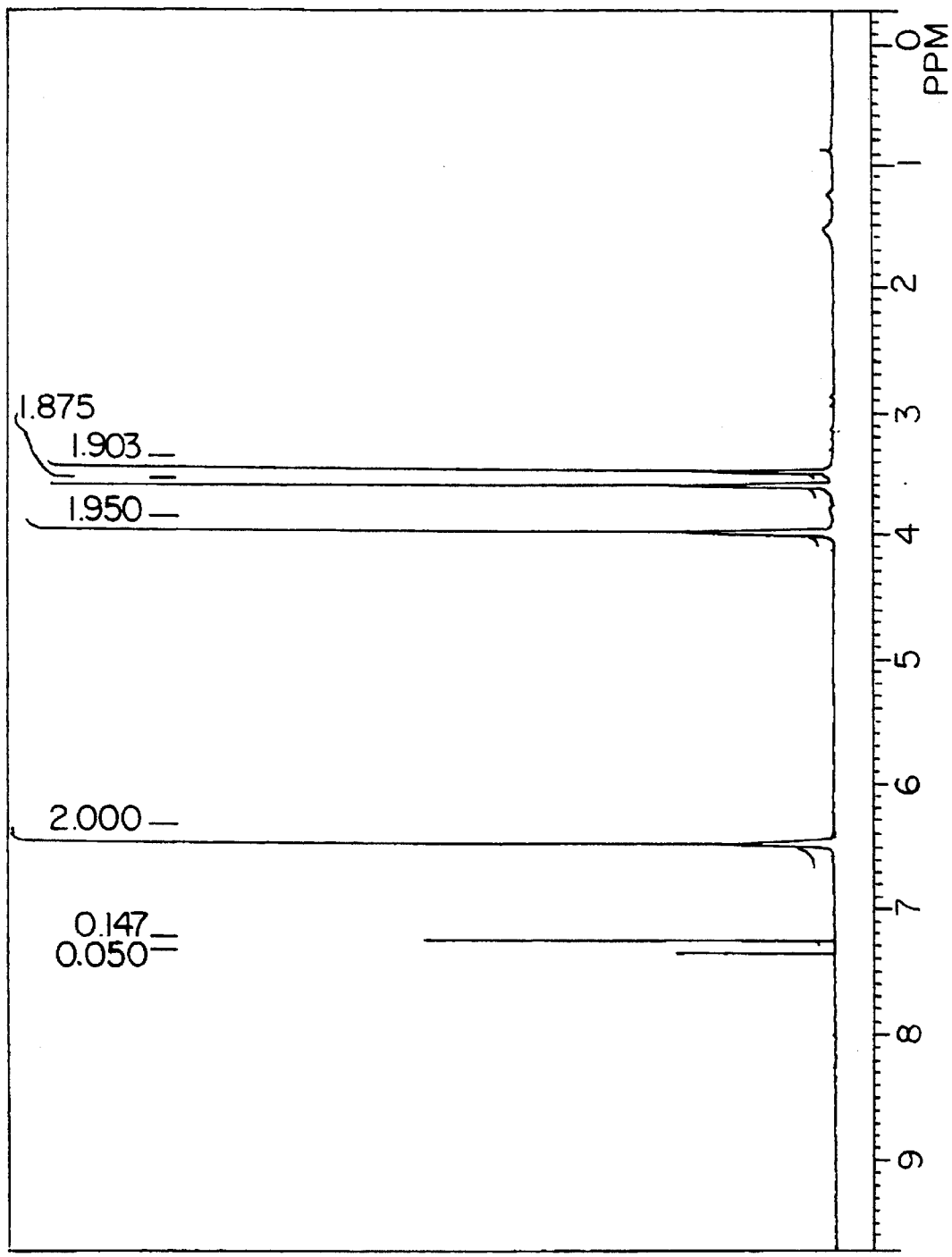
FIG. 2 is a proton magnetic resonance spectral ($^1$H-NMR) chart of the acid chloride.

Furthermore, the σ values of the proton magnetic resonance spectrum ($^1$H-NMR) of the acid chloride were 3.44 to 3.52 (2H,m), 3.58 to 3.64(2H,m), 3.96 to 4.04(2H,m), and 6.44 to 6.52(2H,m) (see FIG. 2).

Figure 3:
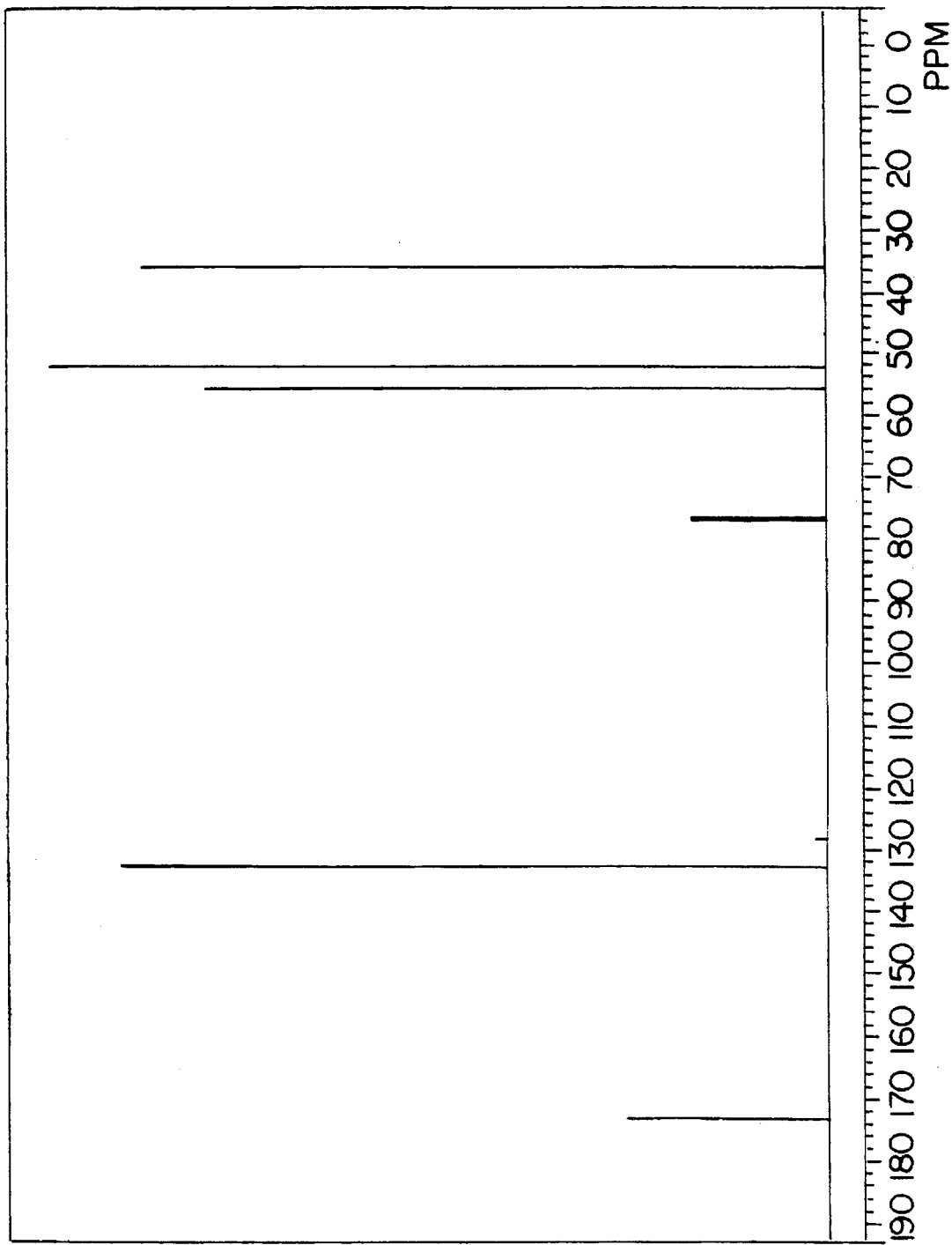
FIG. 3 is a carbon magnetic resonance spectral ($^{13}$C-NMR) chart of the acid chloride.

The σ values of the carbon magnetic resonance spectrum ($^{13}$C-NMR) of the acid chloride were 35.81, 52.32, 55.80, 132.93, 173.03, and 173.09 (see FIG. 3).

Figure 4:
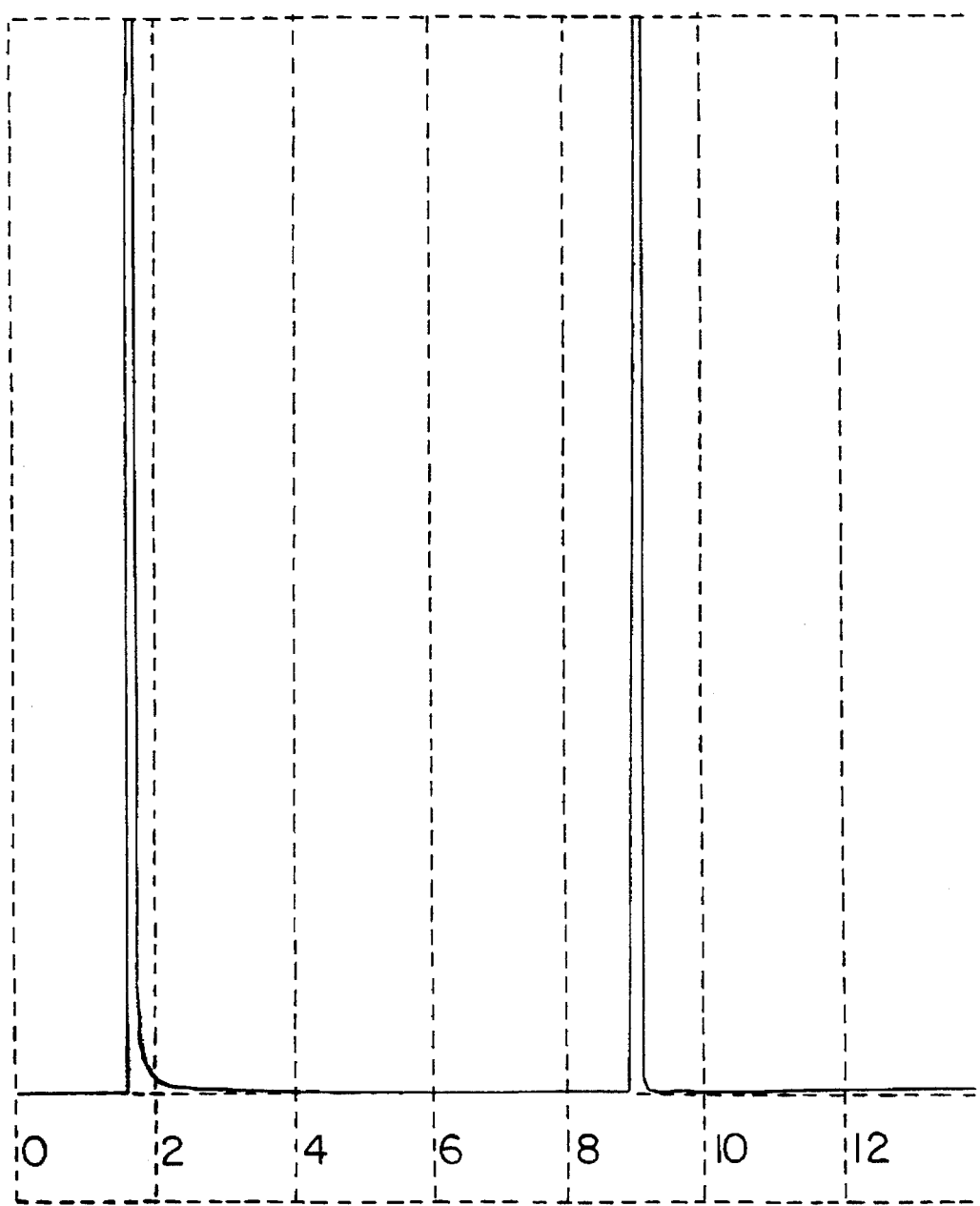
FIG. 4 is a gas chromatographic (GC) chart of the acid chloride esterified with methanol.

When bicyclo[2,2,2]oct-7ene-(2α, 3β,5α,6β)-tetracarbonyl chloride was esterified with methanol and a gas chromatographic (GC) analysis was carried out under the following conditions, the results were as follows. That is, a single peak was observed at a retention time of 9.1 min., and the purity was 100% (see FIG. 4).

Column: DB-1, 0.025 mm (diameter)×29 m, df=0.25 μm.
Column Pressure: 1.5 kg/cm².
Injection Temperature: 250° C.
Column Temperature: 150° to 280° C., 10° C./min.
Detector Temperature: 250° C.
Carrier Gas: He, 40 ml/min.

Also, the result of the elemental analysis was as follows.

Found: C 40.10% H 2.21%

Calculated: C 40.22% H 2.23%

From the above results, the compound obtained was identified as bicyclo[2,2,2]oct-7ene-(2α, 3β,5α,6β)-tetracarbonyl chloride.

The novel acid chloride can be easily produced using bicyclo[2,2,2]oct-7ene-2,3,5,6-tetracarboxylic dianhydride (Aldrich) represented by the following formula as the starting material:

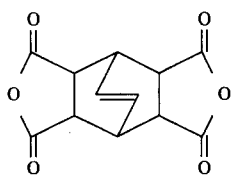

The starting material, bicyclo[2,2,2]oct-7ene2,3,5,6-tetracarboxylic dianhydride is hydrolyzed according to the conventional method to provide a carboxylate or a carboxylic acid and by reacting the product with a chlorinating agent, bicyclo[2,2,2]-oct-7ene-2,3,5,6-tetracarbonyl chloride containing various isomers is obtained. Furthermore, by recrystallizing the compounds obtained, bicyclo[2,2,2]oct-7ene-(2α, 3β,5α,6β)-tetracarbonyl chloride of the present invention can be obtained.

The chlorination reaction is carried out in non-solvent or a non-protonic solvent. As the non-protonic solvent used, hexane, heptane, octane, benzene, toluene, tetrahydroxyfuran (THF), dioxane, etc., can be preferably used, and heptane is particularly suitably used.

Preferred examples of the chlorinating agent are thionyl chloride, phosphorus pentachloride, phosphorus chloride, phosphorus oxychloride, oxalyl chloride, and phosgene although the chlorinating agent used in this invention is not limited to these compounds. For obtaining the best yield, it is preferable that the amount of the chlorinating agent added be from 1 to 5 equivalents, and particularly from 1.2 to 2.0 equivalents to the carboxylic acid group of the bicyclo[2,2,2]-oct-7ene-2,3,5,6-tetracarboxylic acid used.

Moreover, in the present invention, a catalyst for accelerating the reaction with the chlorinating agent can be used. As such a catalyst, dimethylformamide, pyridine, zinc chloride, hexamethylphosphoric triamide (HMPA), etc., can be suitably used.

When a solvent exists, the reaction is carried out at a temperature of from $-70°$ C. to $250°$ C., and preferably from room temperature to the refluxing temperature of the solvent, for 10 minutes to 18 hours.

After completion of the reaction, when the acid chloride-containing solution obtained contains residues, the solution is washed by decantation or filtration, and the solution layer obtained is concentrated under a reduced pressure. Then, by recrystallizing the concentrated residue using a recrystallizing solvent, the novel acid chloride of the present invention can be obtained. As the recrystallizing solvent, heptane or a benzene/hexane series solvent is suitably used but the solvent is not limited to these solvents.

By treating the bicyclo[2,2,2]oct-7ene-2,3,5,6-tetracarboxylic acid obtained by hydrolyzing bicyclo[2,2,2]oct-7ene-2,3,5,6-tetracarboxylic dianhydride with a suitable chlorinating agent and then recrystallizing it as described above, bicyclo[2,2,2]oct-7ene-(2α, 3β,5α,6β)-tetracarbonyl chloride which is the novel acid chloride can be obtained.

Since in the composite reverse osmosis membrane according to the 1st embodiment of the present invention, the thin membrane contains a specific component as the structural component, the composite reverse osmosis membrane has both very high desalinating performance and water-permeating performance by a low-pressure operation and can be suitably used, for example, for the production of fresh water by desalination of brine, seawater, etc., and the production of ultrapure water which is required for the production of semiconductors.

The novel acid chloride which is the 2nd embodiment of the present invention has a high purity as the acid chloride and is a material having very wide utilities as polymeric material-producing raw materials such as crosslinking agents, esterifying agents, amidating agents, acylating agents, etc.

Then, the following examples are intended to illustrate the present invention more practically but not to limit it in any way.

Example 1

An aqueous solution obtained by adding 0.3% by weight of triethylamine and 0.7% by weight of camphor sulfonic acid to an aqueous solution containing 2.0% by weight of m-phenylenediamine and 0.25% by weight of sodium laurylsulfate was contacted with a microporous polysulfone supporting membrane for several seconds and the excessive aqueous solution was then removed to form a layer of the aqueous solution on the supporting membrane.

A hexane solution containing 0.25% by weight of bicyclo[2,2,2]oct-7ene-2,3,5,6-tetracarbonyl chloride containing various isomers thereof was contacted with the surface of the layer formed on the supporting membrane to form a polymer thin membrane on the microporous supporting membrane, whereby a composite reverse osmosis membrane was obtained.

When the performance of the composite reverse osmosis membrane thus obtained was evaluated using brine of pH 6.5 containing 1,500 ppm of sodium chloride at a pressure of 15 kg/cm$^2$, the salt rejection was 99.2% and the flux was 0.7 m$^3$/m$^2$·day.

Example 2

When the composite reverse osmosis membrane obtained in Example 1 was further treated with an aqueous solution of 20 ppm of sodium hypochlorite for 30 minutes, the performance of the composite reverse osmosis membrane evaluated by the same manner as in Example 1 was that the salt rejection was 99.7% and the flux was 0.4 m$^3$/m$^2$·day.

Example 3

By following the same procedure as in Example 1 except that decane was used as the solvent in place of hexane, a composite reverse osmosis membrane was obtained and the performance thereof evaluated by the same manner as in Example 1 was that the salt rejection was 99.5% and the flux was 0.5 m$^3$/m$^2$·day.

Example 4

By following the same procedure as in Example 1 except that an aqueous solution obtained by adding 1.0% by weight of triethylamine and 2.0% by weight of camphor sulfonic acid to an aqueous solution containing 2.0% by weight of m-phenylenediamine and 0.25% by weight of sodium laurylsulfate was used in place of the aqueous amine solution in Example 1, a composite reverse osmosis membrane was obtained. The performance of the composite reverse osmosis membrane evaluated by the same manner as in Example 1 was that the salt rejection was 99.1% and the flux was 0.7 m$^3$/m$^2$·day.

Example 5

By following the same procedure as in Example 4 except that a mixed hexane solution containing 0.25% by weight of bicyclo[2,2,2]oct-7ene-2,3,5,6-tetracarbonyl chloride and 0.25% by weight of 1,2,3,4-cyclopentanetetracarboxylic acid chloride was used as the acid halide solution in Example 4, a composite reverse osmosis membrane was obtained. The performance of the composite reverse osmosis membrane obtained evaluated by the same manner as in Example 4 was that the salt rejection was 99.3% and the flux was 0.5 m³/m²·day.

Example 6

After refluxing 10 g (40.3 mmols) of bicyclo-[2,2,2]-oct-7ene-2,3,5,6-tetracarboxylic dianhydride and 12.9 g (193.5 mmols) of potassium hydroxide in 80 ml of ethanol, the reaction mixture was cooled. After the reaction, ethanol was distilled off, the residue formed was extracted with acidified ether, and the extract (ether layer) was dehydrated with anhydrous magnesium sulfide. The ether layer obtained was concentrated under reduced pressure to provide 7.2 g (yield 63%) of bicyclo[2,2,2]oct-7ene-2,3,5,6-tetracarboxylic acid.

To 3 ml of heptane were added 0.82 g (2.9 mmols) of bicyclo[2,2,2]oct-7ene-2,3,5,6-tetracarboxylic acid, 2.76 g (23.2 mmols) of thionyl chloride and one drop of DMF, and the mixture was then heated at 60° C. for 4 hours. After cooling the reaction mixture obtained, the acid chloride-containing solution was recovered by decantation and the solution layer obtained was distilled under reduced pressure. By recrystallizing the reaction residue obtained from a mixed solvent of benzene and hexane, 0.75 g (yield 73%) of white crystals of bicyclo[2,2,2]oct-7ene-(2α, 3β,5α,6β)-tetracarbonyl chloride were obtained.

The product was identified as bicyclo[2,2,2]oct-7ene-(2α, 3β,5α,6β)-tetracarbonyl chloride by that the absorption wave number (cm⁻¹) of the infrared absorption spectrum was 1790(s) (see FIG. 1), the σ values of the proton magnetic resonance spectra (¹H-NMR) (400 MHz, CDCl) were 3.44 to 3.52(2H,m), 3,58 to 3.64(2H,m), 3.96 to 4.04(2H,m), and 6.44 to 6.52(2H,m) (see FIG. 2), the σ values of the carbon magnetic resonance spectra (¹³C-NMR) were 35.81, 52.32, 55.80, 132.93, 173.03, and 173.09 (see FIG. 3), the product obtained was methylesterified with methanol and the result of analyzing the product by gas chromatography (GC) was single peak (retention time 9.1 min.) (see FIG. 4), and the result of the elemental analysis was that C: 40.10% and H: 2.21% (calculated: C: 40.22% and H: 2.23%).

Example 7

In Example 4, a decane solution containing 0.20% by weight of bicyclo[2,2,2]oct-7ene-(2α, 3β,5α,6β)-tetracarbonyl chloride was used as the acid halide solution. After forming a polymer thin membrane on the microporous supporting membrane as in Example 1, the assembly was heat-treated at 120° C. for 5 minutes to provide a composite reverse osmosis membrane. The performance of the composite reverse osmosis membrane obtained evaluated by the same manner as in Example 1 was that the salt rejection was 99.4% and the flux was 0.7 m³/m²·day.

Example 8

By following the same procedure as in Example 4 except that a hexane solution containing 0.20% by weight of bicyclo[2,2,2]oct-7ene-(2α, 3β,5α,6β)-tetracarbonyl chloride and 0.10% by weight of isophthalic acid chloride was used as the acid halide solution, a composite reverse osmosis membrane was obtained.

The performance of the composite reverse osmosis membrane obtained was that the salt rejection was 99.3% and the flux was 1.2 m³/m²·day.

Furthermore, when the composite reverse osmosis membrane was treated with an aqueous solution of sodium hypochlorite, the performance of the composite reverse osmosis membrane was that the salt rejection was 99.5% and the flux was 1.2 m³/m²·day.

Example 9

By following the same procedure as in Example 4 except that biphenyl-2,2'-dicarboxylic acid chloride was used in place of isophthalic acid chloride in Example 8, a composite reverse osmosis membrane was obtained.

The performance of the composite reverse osmosis membrane was that the acid rejection was 99.8% and the flux was 1.2 m³/m²·day.

Example 10

By following the same procedure as in Example 4 except that 2,6-naphthalenedicarboxylic acid chloride was used in place of isophthalic chloride in Example 8, a composite reverse osmosis membrane was obtained.

The performance of the composite reverse osmosis membrane obtained was that the acid rejection was 99.7% and the flux was 0.4 m³/m²·day.

Example 11

An aqueous solution obtained by adding 2.0% by weight of triethylamine and 4.0% by weight of camphor sulfonic acid to an aqueous solution containing 2.0% by weight of m-phenylenediamine and 0.15% by weight of sodium laurylsulfate was contacted with a microporous polysulfone supporting membrane for several seconds and then the excessive aqueous solution was removed to form a layer of the aqueous solution on the microporous supporting membrane.

A hexane solution containing 0.08% by weight of bicyclo[2,2,2]oct-7ene-(2α,3β,5α,6β)-tetracarbonyl chloride and 0.04% by weight of biphenyl-2,2'-dicarboxylic acid chloride was contacted with the surface of the layer formed on the microporous supporting membrane followed by drying at 120° C. to provide a composite reverse osmosis membrane.

The performance of the composite reverse osmosis membrane obtained evaluated by the same manner as in Example 1 was that the salt rejection was 99.6% and the flux was 0.6 m³/m²·day.

Example 12

When the composite reverse osmosis membrane obtained in Example 11 was further treated with an aqueous solution of 20 ppm of sodium hypochlorite for 30 minutes, the performance of the composite reverse osmosis membrane was increased to that the salt rejection was 99.7% and the flux was 0.7 m³/m²·day.

While the invention has been described in detail and with reference to specific embodiments thereof, it will be apparent to one skilled in the art that various changes and modifications can be made therein without departing from the spirit and scope thereof.

What is claimed is:

1. A novel acid chloride, bicyclo[2,2,2]oct-7ene-(2α,3β, 5α,6β)-tetracarbonyl chloride ($C_{12}H_8O_4Cl_4$) represented by the following formula:

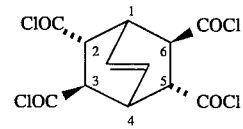

* * * * *